(12) United States Patent
Yan

(10) Patent No.: US 10,145,787 B2
(45) Date of Patent: Dec. 4, 2018

(54) EXCRETA OCCULT BLOOD INSPECTION METHOD AND APPARATUS THEREOF

(71) Applicant: Wellysun Inc., Hsinchu County (TW)

(72) Inventor: Shuo-Ting Yan, Hsinchu County (TW)

(73) Assignee: WELLYSUN INC., Hsinchu County (TW)

( * ) Notice: Subject to any disclaimer, the term of this patent is extended or adjusted under 35 U.S.C. 154(b) by 178 days.

(21) Appl. No.: 15/227,719

(22) Filed: Aug. 3, 2016

(65) Prior Publication Data

US 2017/0212039 A1 Jul. 27, 2017

Related U.S. Application Data

(60) Provisional application No. 62/281,371, filed on Jan. 21, 2016.

(51) Int. Cl.
| | |
|---|---|
| *G01N 21/31* | (2006.01) |
| *G01J 3/02* | (2006.01) |
| *G01N 33/483* | (2006.01) |

(52) U.S. Cl.
CPC ............ *G01N 21/31* (2013.01); *G01J 3/0264* (2013.01); *G01N 33/4833* (2013.01); *G01N 2201/12* (2013.01)

(58) Field of Classification Search
CPC ............... G01N 21/31; G01N 33/4833; G01N 2201/12; G01J 3/0264
See application file for complete search history.

(56) References Cited

U.S. PATENT DOCUMENTS

| | | | | |
|---|---|---|---|---|
| 5,184,359 | A | * | 2/1993 | Tsukamura ........ A61B 5/02241 4/314 |
| 7,223,604 | B1 | | 5/2007 | Liu et al. |
| 9,816,930 | B2 | * | 11/2017 | Moriyama ......... G01N 21/6456 |
| 9,828,755 | B1 | * | 11/2017 | Clements .................. E03D 9/08 |
| 2004/0068230 | A1 | * | 4/2004 | Estes .................... A61B 5/0002 604/154 |
| 2005/0261605 | A1 | * | 11/2005 | Shemer ................ A61B 10/007 600/573 |
| 2007/0064220 | A1 | * | 3/2007 | Stock ................... G01N 21/251 356/73 |
| 2009/0038064 | A1 | * | 2/2009 | Rigas ..................... A47K 13/24 4/242.1 |
| 2012/0015445 | A1 | * | 1/2012 | Kellner ............. G01N 21/6428 436/172 |
| 2013/0273524 | A1 | | 10/2013 | Ehrenkranz |

(Continued)

FOREIGN PATENT DOCUMENTS

CN 104254621 A 12/2014
JP A_1998-339728 A 12/1998

*Primary Examiner* — Que T Le
*Assistant Examiner* — Jennifer Bennett
(74) *Attorney, Agent, or Firm* — Chun-Ming Shih

(57) ABSTRACT

This invention discloses an excreta occult blood inspection method and the apparatus thereof. The inspection method comprises the following steps. At least one light source is provided to emit at least one light to illuminate excreta to produce at least one specimen light. At least one photosensitive unit is provided to receive the specimen light and generate a detected data. An analysis processor is provided to receive and analyze the detected data to produce an analysis data. Above-mentioned method and apparatus can make excreta occult blood inspection become efficient and convenient.

20 Claims, 12 Drawing Sheets

(56) References Cited

U.S. PATENT DOCUMENTS

2014/0147924 A1* 5/2014 Wheeldon .............. G01N 21/75
                                              436/63
2017/0303901 A1* 10/2017 Sekine ............... A61B 10/0038

* cited by examiner

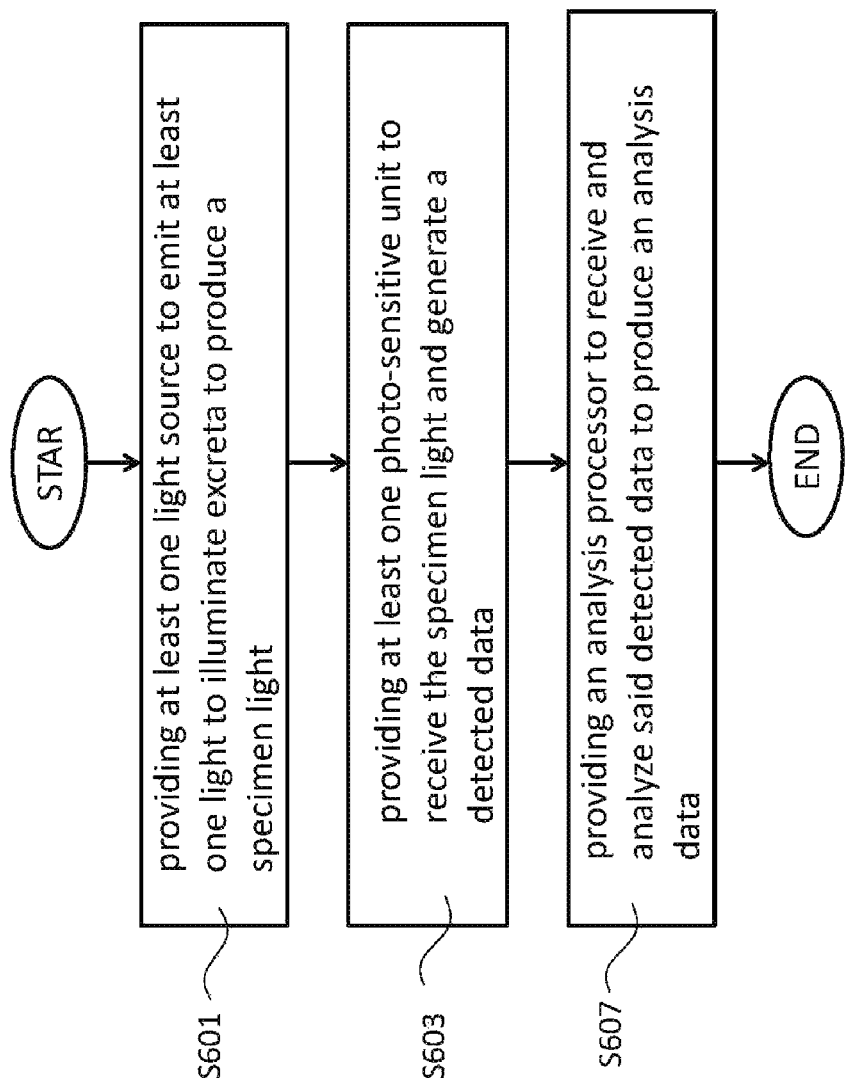

EXCRETA OCCULT BLOOD INSPECTION METHOD AND APPARATUS THEREOF

REFERENCE TO RELATED APPLICATIONS

This application is based on Provisional application Ser. No. 62/281,371, filed Jan. 21, 2016, currently pending.

FIELD OF THE INVENTION

The present invention relates to an excreta occult blood inspection method and an apparatus thereof. Excreta are illuminated by a light source for producing a specimen light, and the specimen light is collected by a photo-sensitive unit for producing a detected data. The excreta may be judged whether it comprises an occult blood or not by analyzing the detected data.

BACKGROUND

Lots of diseases is associate with excreta occult blood, so excreta occult blood can be seen as an alarm to remind people to inspect and check health status.

Traditional excreta occult blood inspection method is complex and inconvenient. People often need to spend lots of time to go to a hospital or inspection agency for inspecting excreta occult blood. On the other hand, most of people do not like to touch excreta, but there is high probability to touch excreta when collecting and sampling excreta as a specimen. It is one of the main reasons that people resist to perform excreta occult blood inspection frequently and periodically.

FIG. 1A to FIG. 1C are inspection flow diagrams of a conventional excreta occult blood inspection method. User may be asked to insert a sampler 11 into excreta after patients or subjects excreting excreta 13 to let portion of the excreta embed in the collection groove 111 of the sampler 11, as shown in FIG. 1A. Afterward, user needs to insert the collection groove 111 into a thinner 15 for mixing the excreta 13 and the thinner 15 evenly, as shown in FIG. 1B, and then drop the thinner 15 comprising the excreta 13 on the testing area 173 of the reagent card 17, as shown in FIG. 1C. Finally, User needs to wait several minutes and then check the number and position of color bands shown in the result area 171 of the reagent card 17 to judge the inspection result, which is negative reaction, positive reaction or invalid reaction.

The above mentioned method is complex and inconvenient, and the method has several disadvantages: the collected excreta 13 is only a little portion of the whole excreta 13; people may touch the excreta 13 in the collection process; people cannot know the inspection result immediately; and the reagent card 17 is not universal and cannot be obtained easily. Therefore, the prior method is not an ideal method for people to perform excreta occult blood inspection by themselves.

SUMMARY

It is one object of the present invention to provide an excreta occult blood inspection method. A specimen light produced by excreta after being illuminated by a light source is collected by a photo-sensitive unit. The photo-sensitive unit will generate a detected data, which will be analyzed for checking whether the excreta comprising occult blood or not. There is no article need to be used to touch the excreta, and the inspection region of the excreta can be enlarged to improve the accuracy of the inspection result, which can inform users immediately.

It is another object of the present invention to apply the above mentioned excreta occult blood inspection method to an excreta occult blood inspection apparatus, through which the occult blood inspection process can be simplified. On the other hand, users do not need to use any excreta sampler, and it will improve the occult blood inspection willingness of users. When the excreta occult blood inspection apparatus is a handheld device, the inspection location and time will not be limited. For example, the handheld excreta occult blood inspection apparatus can apply to toilet, toilet paper, diaper or other article attached with excreta easily. When the excreta occult blood inspection apparatus is a stationary occult blood inspection module, which can be installed on an excreta collector and/or a peripheral device of the excreta collector, users can perform the occult blood inspection just after urinating or defeating. The inspection process is easy and convenient. Users do not need to use any excreta sampler, and it will improve the occult blood inspection willingness of users.

It is another object of the present invention to apply an analysis processor and display unit of an existed electrical product in the market as an analysis process and display of the excreta occult blood inspection apparatus. In this way, the whole set-up cost and dimension of the excreta occult blood inspection apparatus can be reduced.

For achieving the above object, the present invention provides an excreta occult blood inspection method comprising the following steps: providing at least one light source to emit at least one light to illustrating excreta to produce a specimen light; providing at least one photo-sensitive unit to receive the specimen light and generate a detected data; and providing an analysis processor to receive and analyze the detected data to produce an analysis data.

For achieving the above object, the present invention provides an excreta occult blood inspection apparatus for inspecting occult blood of excreta. The excreta occult blood inspection apparatus comprises a case; a first light source fixed on the case; a user interface connected with the first light source for starting the first light source up to emit a first light, wherein the first light illuminates the excreta, which will produce a first specimen light after being illuminated; a photo-sensitive unit disposed in the case for receiving the first specimen light and generating an detected data; an analysis processor receiving and analyzing the detected data from the photo-sensitive unit for producing an analysis data; and a display unit electrically connected with the analysis processor for displaying the analysis data.

For achieving the above object, the prevent invention provides an excreta occult blood inspection apparatus for inspecting occult blood of excreta. The excreta occult blood inspection apparatus comprises a case; a first light source fixed on the case; a user interface connected with the first light source for starting the first light source up to emit a first light illuminating the excreta, and the excreta will produce a first specimen light after being illuminated; a photo-sensitive unit fixed on the case for receiving the first specimen light and generating an detected data; and a remote electrical device, comprising: an analysis processor disposed on the remote electrical device for receiving and analyzing the detected data from the photo-sensitive unit to generate an analysis data; and a display unit disposed on the remote electrical device and electrically connected with the analysis processor for displaying the analysis data.

BRIEF DESCRIPTION OF THE DRAWINGS

The structure as well as preferred modes of use, further objects, and advantages of this invention will be best understood by referring to the following detailed description of some illustrative embodiments in conjunction with the accompanying drawings, in which:

FIG. 2 is a flow chart of an excreta occult blood inspection method according to one embodiment of the present invention.

DETAILED DESCRIPTION OF THE PREFERRED EMBODIMENTS

Figure 1C:
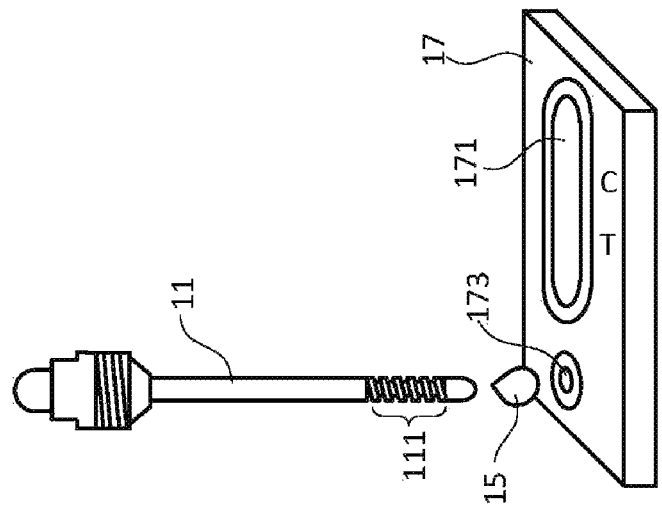
FIG. 1A to FIG. 1C are inspection flow diagrams of a conventional excreta occult blood inspection method.
Figure 1B:
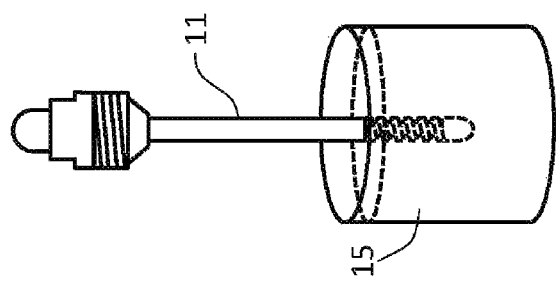
Figure 1A:
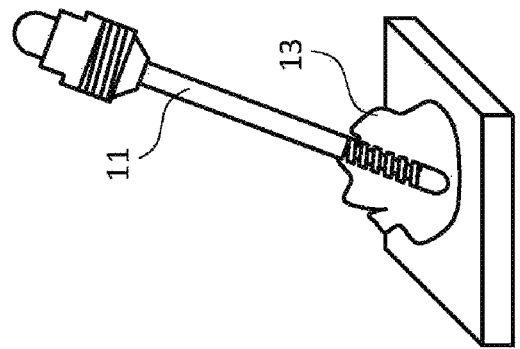

The excreta mentioned in the present invention comprises faeces, urine, phlegm, feces or secretions, and occult blood mentioned in the present invention is blood of humans or animals comprised in excreta. Lots of diseases associate with excreta occult blood. For example, the fecal occult blood may associate with colorectal cancer, urine occult blood may associate with kidney cancer, ureter cancer or bladder cancer; and occult blood in phlegm may associate with bronchitis or lung cancer. By the excreta occult blood inspection method and apparatus thereof disclosed in the present invention, users can perform excreta occult blood inspection fast and convenient, and the health status can be monitored at any time.

FIG. 2 is a flow chart of an excreta occult blood inspection method according to one embodiment of present invention. The excreta occult blood inspection method comprises step 601, step 603 and step 607. At least one light source is provided to emit at least one light to illuminate excreta to produce at least one specimen light, as shown in step S601. At least one photo-sensitive unit is provided to receive the specimen light and generate a detected data, as shown in step S603. An analysis processor is provided to receive and analyze the detected data to produce an analysis data, as shown in step S607.

The photo-sensitive unit mentioned in the present invention denotes that a component which can distinguish and detect light intensity distribution at different wavelength, such as photo sensor, photo diode, charge-coupled device (CCD), or CMOS image sensor. In one embodiment of the present invention, the specimen light produced by illuminated excreta is a fluorescent light, an excitation light and/or a reflective light.

The above mentioned excreta occult blood inspection method can be applied to a handheld excreta occult blood inspection apparatus, which is easy to be carried. The handheld excreta occult blood inspection apparatus make the occult blood inspection do not be limited with time and location. For example, a handheld occult blood can be easily applied to a toilet, an urinal, a diaper, a spittoon, a toilet paper, or other article attached with excreta.

On the other hand, the above mentioned excreta occult blood inspection method can also be applied to a stationary occult blood inspection module, which can be installed on an excreta collector and/or a peripheral devices of the excreta collector, and users can perform occult blood inspection just after excreting excreta. It is very convenient for users, who do not need to use any excreta sampler, and users can avoid touching excreta.

The excreta collector mentioned in the present invent denotes a device which can be used to collect faeces, urine, phlegm, feces or secretions, such as a sitting toilet, a squat toilet, a bedpan, an urinal, a spittoon and so on. The peripheral devices of the excreta collector denotes a device which can be attached to the excreta collector, such as a toilet lid, an electrical toilet seat, a bedpan lid, a urinal lid and so on.

Figure 3:
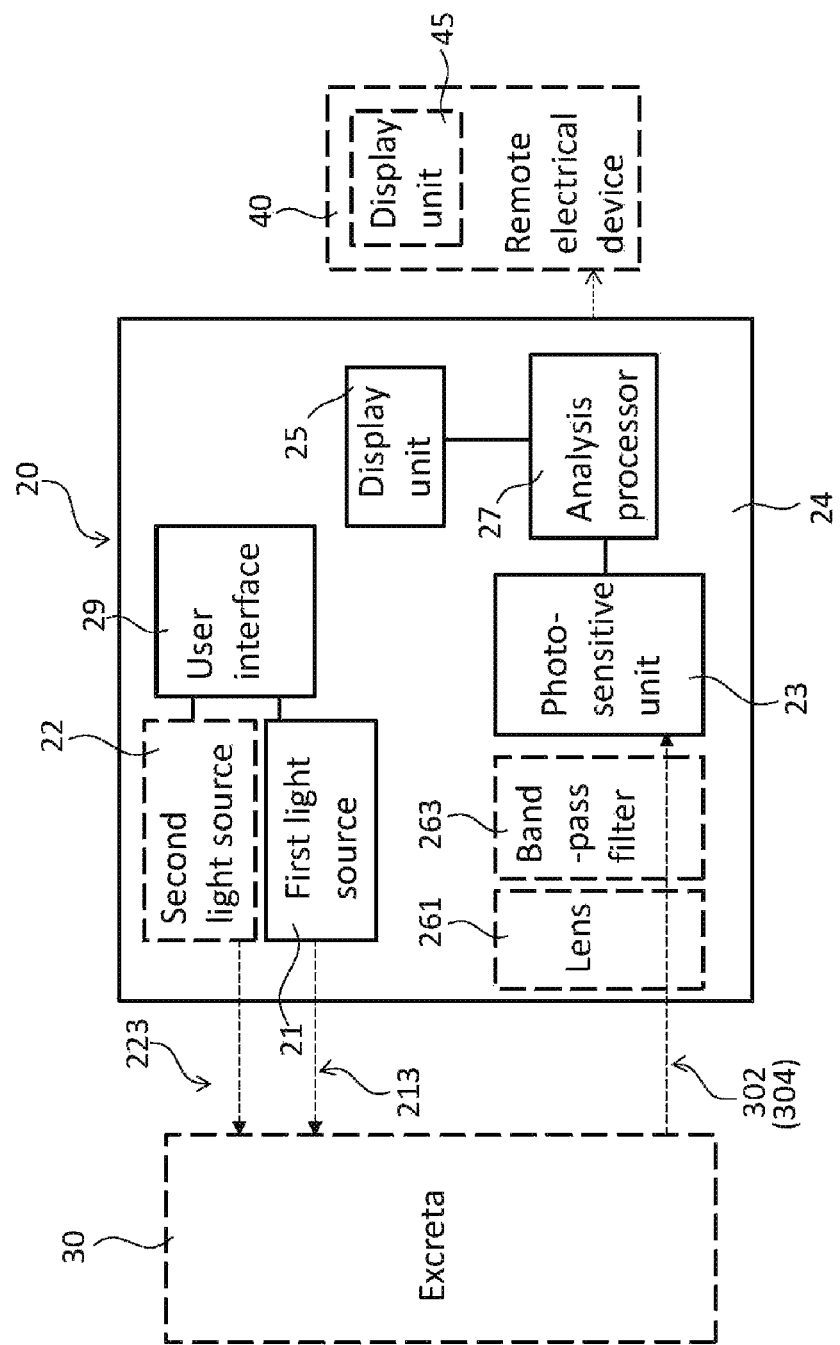
FIG. 3 is a block diagram of an excreta occult blood inspection apparatus according to one embodiment of the present invention.
Figure 4:
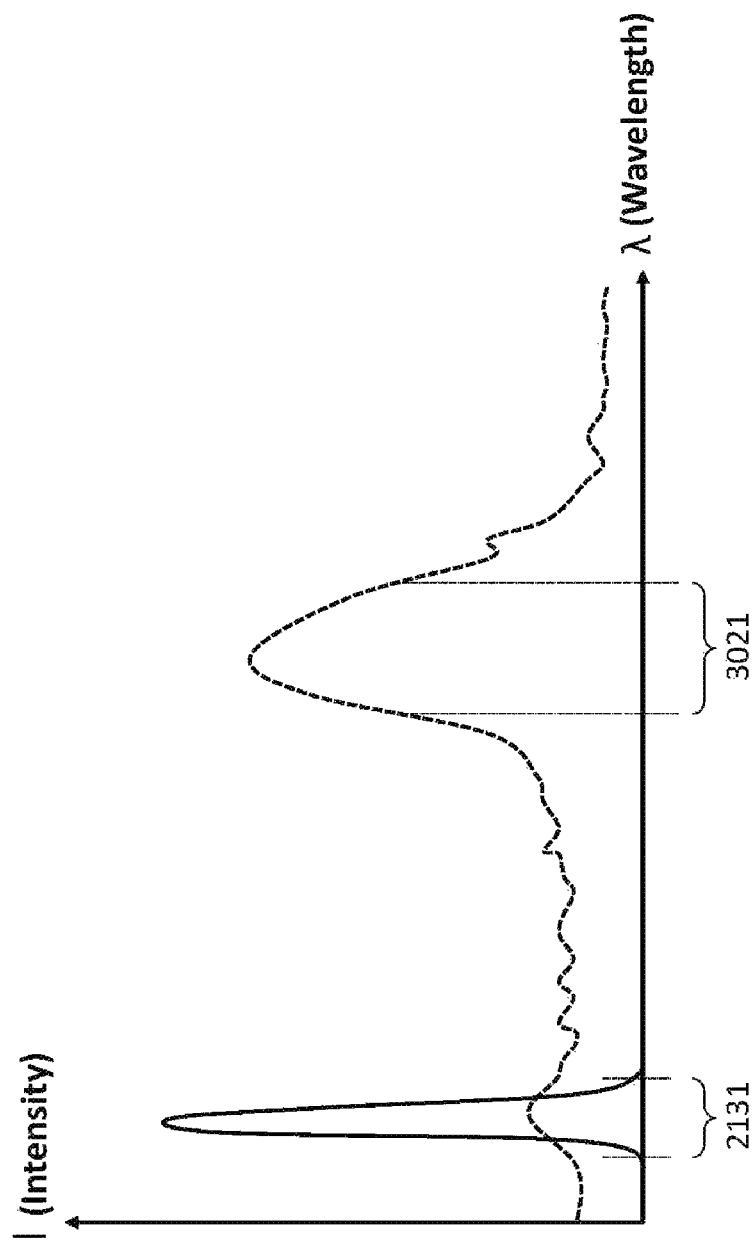
FIG. 4 is a wavelength spectrum diagram of the first light and the first specimen light of an excreta occult blood inspection apparatus.

FIG. 3 is a block diagram of an excreta occult blood inspection apparatus according to one embodiment of the present invention, and FIG. 4 is a wavelength spectrum diagram of the first light and the first specimen light of the excreta occult blood inspection apparatus of the present invention. The occult blood apparatus 20 comprises a case 24, a first light source 21, a photo-sensitive unit 23, an analysis processor 27, a user interface 29 and a display unit 25.

The case 24 can be a handheld case for carrying easily or a stationary case, which suits to be installed on an excreta collector or a peripheral devices of the excreta collector, such as a toilet, a toilet seat and/or toilet lid. The mode of carrying out the case 24 will be illustrated in the following embodiments.

The first light source 21 is used to produce a first light 213 with a first wavelength range 2131, wherein the first light 213 can be used to project and illuminate on the excreta 30. The first light source 21 can be disposed inside or on the outer surface of the case 24.

The excreta 30 will produce a first specimen light 302 with a peak wavelength within a second wavelength range 3021 after being illuminated by the first light 213, as shown in FIG. 4, if the excreta 30 comprises occult blood.

In one embodiment in the present invention, the wavelength of the first wavelength range 2131 is shorter than the wavelength of the second wavelength range 3021. For example, the wavelength of the first light 213 may be around 407 nm, and the first specimen light 302 generated by the excreta 30 may comprise a peak wavelength around 613 nm. The wavelength 407 nm and 613 nm are only one embodiment of the present invention and are not the limitation of the invention. In other embodiment of the invention, the wavelength of the first light 213 may be different from 407 nm, and the peak wavelength of the first specimen light 302 may be different from 613 nm.

The photo-sensitive unit 23 is used to receive the first specimen light 302 generated by the excreta 30 after being illuminated by the first light 213 and generate a detected data. The detected data can be a light intensity value within a specific wavelength range, a spectrum, or other information about the wavelength. The photo-sensitive unit 23 is installed inside the case 24 or on the surface of the case 24 and located on the transmission path of the first specimen light 302. The location of the photo-sensitive unit 23 cannot interfere with the transmission path of the first light 213 to insure that the intensity of the first light 213 illuminated on the excreta 30 will not be weakened. The location of the photo-sensitive unit 23 also need to avoid blocking the first light 21 to insure that the first light can illuminate on the excreta 30.

The user interface 29, which is electrically connected with the first light source 21, is disposed on the surface of the case 24. Users can issue a start signal by the user interface 29 to start the first source 21 up to emit a first light 23 for illuminating the excreta 30. The user interface 29 can be a push button, a switch, a touch panel or other interfaces that users can operate.

The analysis processor 27 installed inside the case 24 is used to receive and analyze the detected data for producing an analysis data. The analysis data can be a value, an occult blood level, a history occult blood trend or a data with other type. For example, when the detected data receiving by the photo-sensitive unit 23 is a spectrum, the analysis processor 27 can only capture the data within the second wavelength range 3021 and ignore the invalid data, such as noise, by an algorithm. Then the analysis processor 27 integrates the data within the second wavelength range 3021 and transfers it as a light intensity value, which can be separated as several levels, such as five levels: "not detected", "light", "medium", "serious" and "very serious".

The display unit 25 installed inside the case 24 or on at least one surface of the case 24 is used to receive and/or display the analysis data produced by the analysis processor 27. In one embodiment of the present invention, the display unit 25 can be a monitor, such as a LCD screen, touch panel, seven-segment display, light-emitting diode or other components, which can display the analysis data. For example, when the analysis processor 27 separates the analysis data as five levels, the five levels can be displayed with roman numerals 1 to 5 by a seven-segment display. The five levels also can be displayed by light-emitting diodes, and each level can be represented by the corresponding numbers of the light-emitting diodes which are powered-on. In this way, users can realize the level of occult blood easily and then judge whether to perform a further inspection in a hospital or not.

In one embodiment of the present invention, the occult blood apparatus 20 can further send the analysis data to a remote electrical device 40, which can be a smart phone, a smart bracelet, a pad, a computer, a server, a database and so on. In one embodiment of the present invention, the remote electrical device 40 may comprise a display unit 45, and the analysis data can be displayed by the display unit 45 of the remote electrical device 40. In this way, users can read the analysis data by the remote electrical device 40, and the analysis data can be further stored in the remote electrical device 40 each time after inspecting for recording and monitoring history occult blood trend. However, the remote electrical device 40 is not the necessary member of the present invention, and it will not limit the scope of rights of the present invention.

In one embodiment of the present invention, the excreta occult blood inspection apparatus 20 can also comprise a second light source 22 installed inside the case 24 or on the surface of the case 24. The second light source 22 is used to produced a second light 223 with a third wavelength range projecting and illuminating on the excreta 30, and the excreta 30 will produce a second specimen light 304 after being illuminated by the second light. If the excreta 30 comprises occult blood, the excreta 30 will generate the second specimen light 304 with a peak wavelength within a fourth wavelength range, and the wavelength of the third wavelength range is shorter than the wavelength of the fourth wavelength range.

For example, the wavelength of the second light 223 may be around 540 nm, and the second specimen light 304 generated by the excreta 30 may comprise a peak wavelength around 630 nm. The wavelength 540 nm and 630 nm is only one embodiment of the present invention, and it does not limit the scope of rights of the present invention. In other embodiment of the invention, the wavelength of the second light 223 may be different from 540 nm, and the peak wavelength of the second specimen light 304 may be different from 630 nm.

In one embodiment of the present invention, the excreta occult blood inspection apparatus 20 may further comprise a band-pass filter 263 installed inside the case 24, and the band-pass filter 263 is located on the path that the first specimen light 302 and/or the second specimen 304 light transmits to the photo-sensitive unit 23, as shown in FIG. 3. The band-pass filter 263 is used to filter the first specimen light 302 and/or the second specimen light 304 for enhancing the available signal to noise ratio (S/N Ratio), and thus the accuracy of the analysis data produced by the analysis processor 27 can be improved.

For example, when the second wavelength range and the fourth wavelength range are around 607 nm and 630 nm individually, a band-pass filter 263 can be used to select light whose wavelength range is from 600 nm to 650 nm. It means that the light whose wavelength range is from 600 nm to 650 nm can passes through the band-pass filter 263 while the visible light and the ultraviolet light whose wavelength is out of 600 nm to 650 nm will be filtered for removing the noise coming from the environment. The band-pass filter 263, which can select the light from 600 nm to 650 nm, is only an embodiment in the present invention, and it does not limit the scope of rights of the present invention.

In one embodiment of the present invention, the excreta occult blood inspection apparatus 20 may further comprise a lens 261 installed inside the case 24, and the lens 261 is located on the path that the first specimen light 302 and/or the second specimen 304 light transmits to the photo-sensitive unit 23, as shown in FIG. 3. The lens 261 is used to collect and transmit the first specimen light 302 and/or the second specimen light 304 to the photo-sensitive unit 23 efficiently for insuring the light intensity of the first specimen light 302 and/or the second specimen light 304 illuminating on the photo-sensitive unit.

The lens 261 and the band-pass filter 263 can be used at the same time, or even more a band-pass coating can be coated on the lens 261 surface to make lens 261 become a band-pass filter 263, which can filter the noise coming from the environment and enhance the available signal to noise ration of the detected data produced by the photo-sensitive unit 23. However, the lens 261 and the band-pass filter 263 are not the necessary members of the present invention, and it will also not limit the scope of rights of the present invention. In other words, the excreta occult blood inspection apparatus 20 can be applied without the lens 261 and/or the band-pass filter 263.

In one embodiment of the present invention, the first light 213 emitted by the first light source 21 and/or the second light 223 emitted by the second light source 22 can be a discontinuous modulated light, such as a discontinuous frequency modulated light. When using a discontinuous frequency modulated light to illuminate the excreta 30, the first specimen light 302 and/or the second specimen light 304 will also be a discontinuous frequency modulated light. The analysis processor 27 can only capture the signal comprising the specific frequency and modulation features from the detected data according to the frequency and modulation features of the first light 213 and/or the second light 223. In this way, the accuracy of the analysis data can be improved by removing the interfere coming from the environment.

Figure 5:
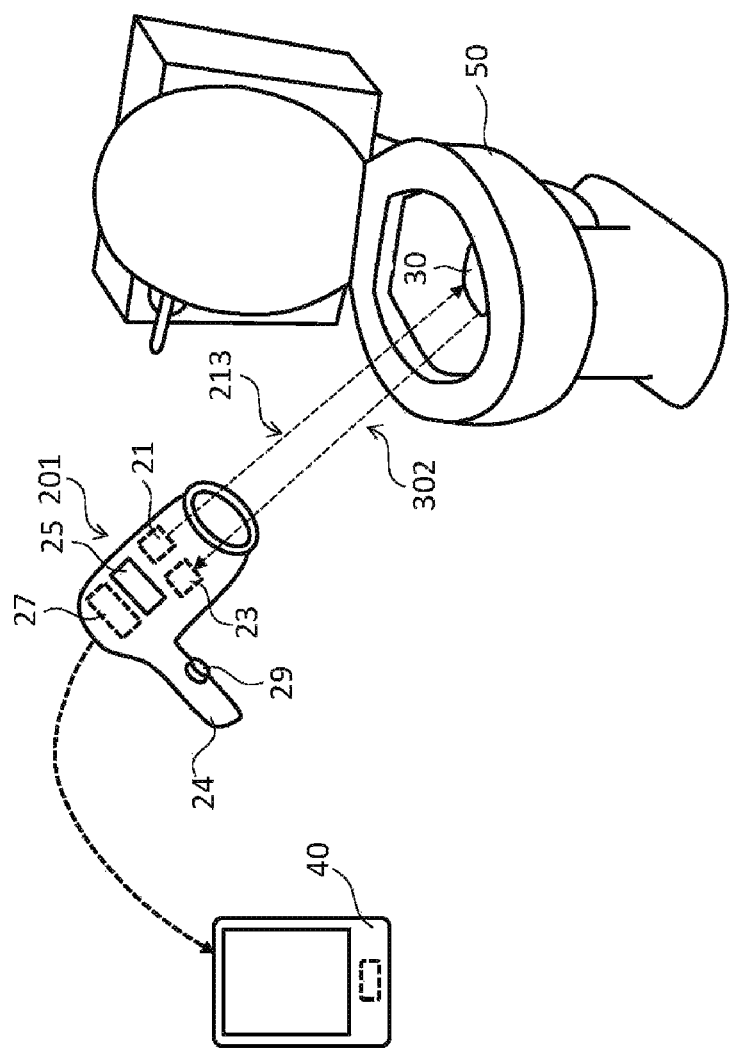
FIG. 5 is a schematic structure diagram of a handheld excreta occult blood inspection apparatus according to one embodiment of the present invention.

FIG. 5 is a schematic structure diagram of a handheld excreta occult blood inspection apparatus according to one embodiment of the invention. The handheld excreta occult blood inspection apparatus 201, which is similar to the excreta occult blood inspection apparatus 20, comprises a case 24, a user interface 29, a first light source 21, a photo-sensitive unit 23, a display unit 25 and an analysis processor 27. The user interface 29 is electrically connected with the first light source 21, and the analysis processor 27 connected with the photo-sensitive unit 23 and the display unit 25. The case 24 in this embodiment is a handheld case, and the user interface 29 and the display unit 25 are installed on at least one surface of the case 24 while the first light source 21, the photo-sensitive unit 23 and the analysis processor 27 are installed inside the case 24. Although the first light source 21 is installed inside the case 24 in this embodiment, it is not the limitation of the location of the first light source 21. The first light source 21 can be installed on the surface of the case 24 in different embodiment.

The principle of the handheld excreta occult blood inspection apparatus 201 is similar to the excreta occult blood inspection apparatus 20. The user interface 29 emits a start signal to the first light source 21, and then the first light source 21 emits a first light 213 to illuminate excreta 30 in an excreta collector 50 according to the start signal. The excreta 30 will produce a first specimen light 302 after being illuminated by the first light 213. The photo-sensitive unit 23 is used to receive the first specimen light 302 and generate a detected data, and the analysis processor 27 is used to receive and analyze the detected data to produce an analysis data.

In one embodiment of the present invention, the handheld excreta occult blood inspection apparatus 201 can be connected with a remote electrical device 40 and send the analysis data to the remote electrical device 40 for users to check or record the analysis data.

Figure 6:
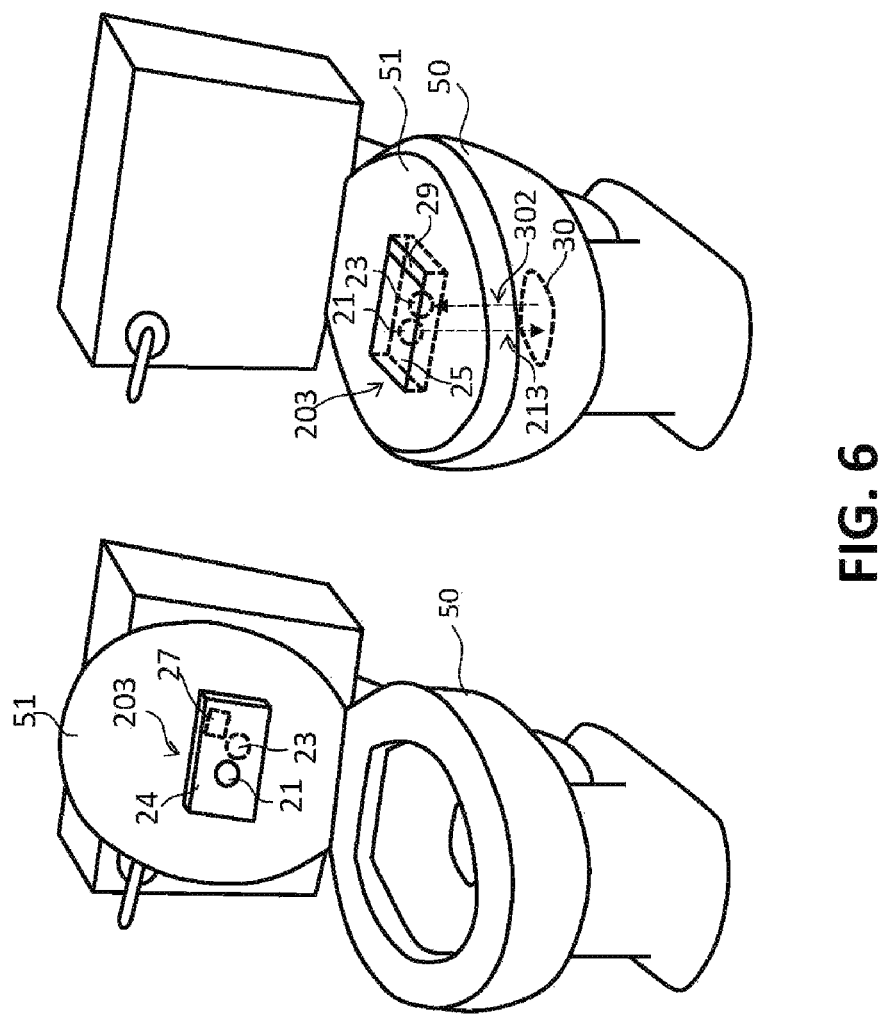
FIG. 6 is a schematic structure diagram of a stationary excreta occult blood inspection module according to one embodiment of the present invention.

FIG. 6 is a schematic structure diagram of a stationary excreta occult blood inspection module according to one embodiment of the invention. The stationary excreta occult blood inspection module 203 can be installed on an excreta collector 50 and or a lid 51. For example, the excreta collector 50 is a sitting toilet, and the lid 51 is a toilet lid. The mechanism structure of the stationary excreta occult blood inspection module 203 is similar to the excreta occult blood inspection apparatus 20. The stationary excreta occult blood inspection module 203 comprises a case 24, a user interface 29, a first light source 21, a photo-sensitive unit 23, a display unit 25 and an analysis processor 27. The user interface 29 is electrically connected with the first light source 21, and the analysis processor 27 is connected with the photo-sensitive unit 23 and the display unit 25.

In one embodiment of the present invention, the stationary occult blood module 203 can be installed on the lid 51. For example, the stationary occult blood module 203 is run through the lid 51. The display unit 25 and the user interface 29 can be disposed on a first surface of the lid 51, such as the top surface of the lid 51, and the first light source 21 and the photo-sensitive unit 23 is disposed on a second surface of the lid 51, such as the bottom surface of the lid 51. When the lid 51 is covered on the excreta collector 50, the second surface will face the excreta collector 50 and/or the excreta 30. In this way, the emitting orientation of the first light 213 emitted by the first light source 21 will face the excreta 30 inside the excreta collector 50, and the photo-sensitive unit 23 can receive the first specimen light 302. Otherwise, the display unit 25 and the user interface 29 will be exposed on the lid 51, and thus users can operate the user interface 29 conveniently and read the analysis data through the display unit 25.

Figure 7:
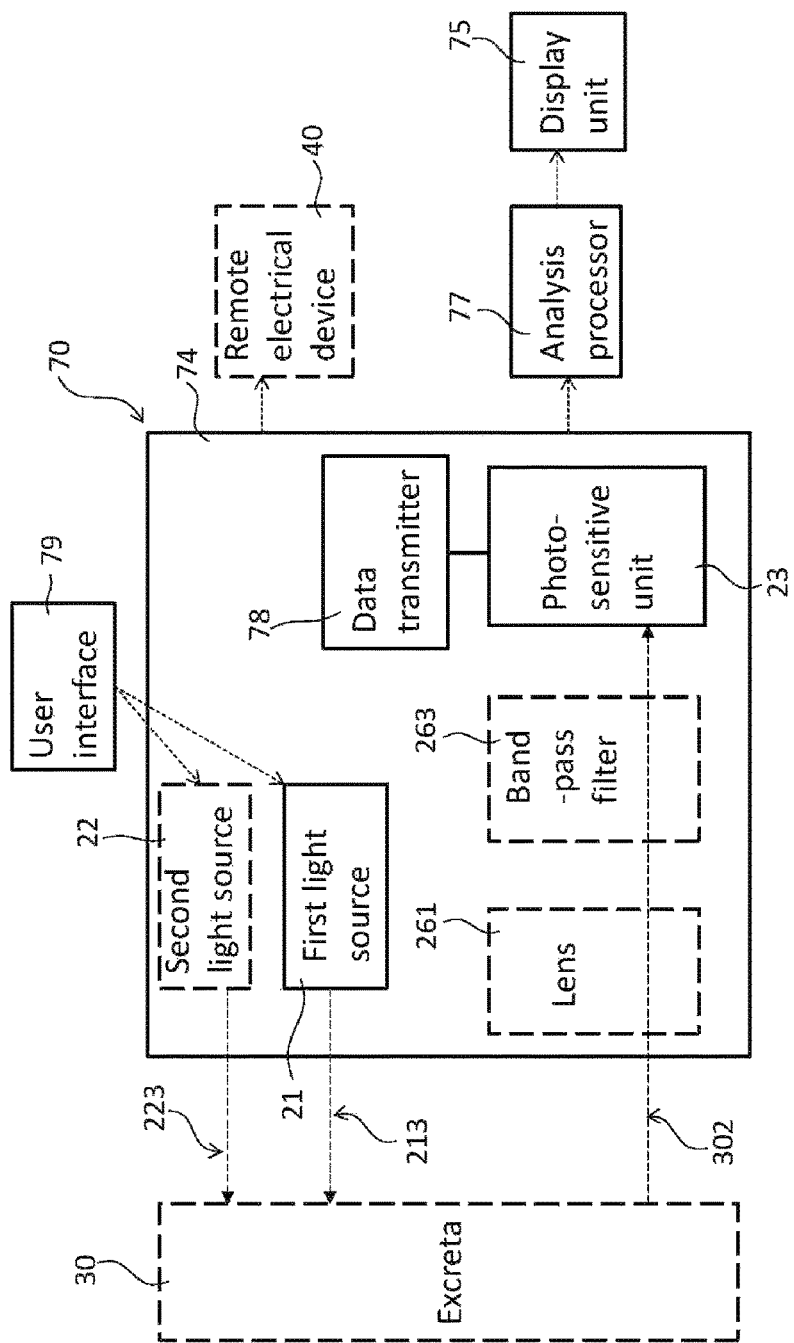
FIG. 7 is a block diagram of an excreta occult blood inspection apparatus according to another embodiment of the present invention.

FIG. 7 is a block diagram of an excreta occult blood inspection apparatus according to another embodiment of the invention. The excreta occult blood inspection apparatus 70 comprises a case 74, a first light source 21, a photo-sensitive unit 23, a data transmitter 78, an analysis processor 77, a display unit 75 and a user interface 79. The first light source 21 and the photo-sensitive unit 23 are installed on the case 74, and the data transmitter 78 is installed inside the case 74. The display unit 75 and the user interface 79 are not installed on the case 703. The data transmitter 78 and the photo-sensitive unit 23 are electrically connected with each other, and the display unit 75 and the analysis processor 77 are electrically connected with each other. The user interface 79 and the first light source 21 are electrically connected with each other. Although the analysis processor 77 is independent of the case 74 for illustration in this embodiment, however, the analysis processor 77 can be dependent or independent of the case 74 in real application.

In this embodiment, users can start the first light source 21 up by the user interface 79 independent of the case 74 and make the first light source 21 emits the first light 213 to project and illuminate on the excreta 30, and the excreta 30 will produce a first specimen light 302 after being illuminated. The photo-sensitive unit 23 will receive the first specimen light 302 and generate a detected data. The data transmitter 78 receives the detected data generated by the photo-sensitive unit 23 and sends it to the analysis processor 77 outside the case 74. The analysis processor 77 will analyze the detected data to produce an analysis data and send the analysis data to the display unit 75 for displaying. In different embodiment in the present invention, the excreta occult blood inspection apparatus 70 can further comprises a second light source 22, a lens 261 and/or a band-pass filter 263. The mechanism structure and function of the second light source 22, lens 261 and/or band-pass filter 263 have been described in the above embodiment, and it will not be repeated here.

In one embodiment of the present invention, the data transmitter 78 also can be used to receive and transfer the detected data sent by the photo-sensitive unit 23, and the detected data can be transferred to a format that the analysis processor 77 can deal with.

Figure 8:
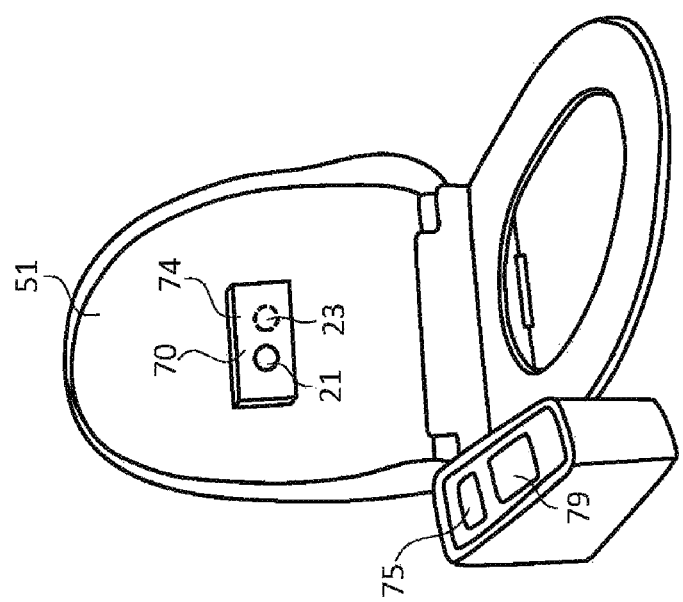
FIG. 8 is a schematic structure diagram of a stationary excreta occult blood inspection module according to another embodiment of the present invention.

FIG. 8 is a schematic structure diagram of a stationary excreta occult blood inspection module according to another embodiment of the invention. In one embodiment of the present invention, the case 74, the first light source 21 and the photo-sensitive unit 23 is disposed on the lid 51, wherein the first light source 74 and the photo-sensitive unit 23 are disposed on the case 74. The user interface 79 and the display unit 75, which are independent of the case 74 and/or the lid 51, are not disposed on the case 74 and/or the lid 51. In this way, users can operate the user interface 79 and read the analysis data from the display unit 75 conveniently. The data transmitter 78 is disposed inside the case 74, and the analysis processor 77 can be disposed on the case 74 or not disposed on the case 74.

Figure 9:
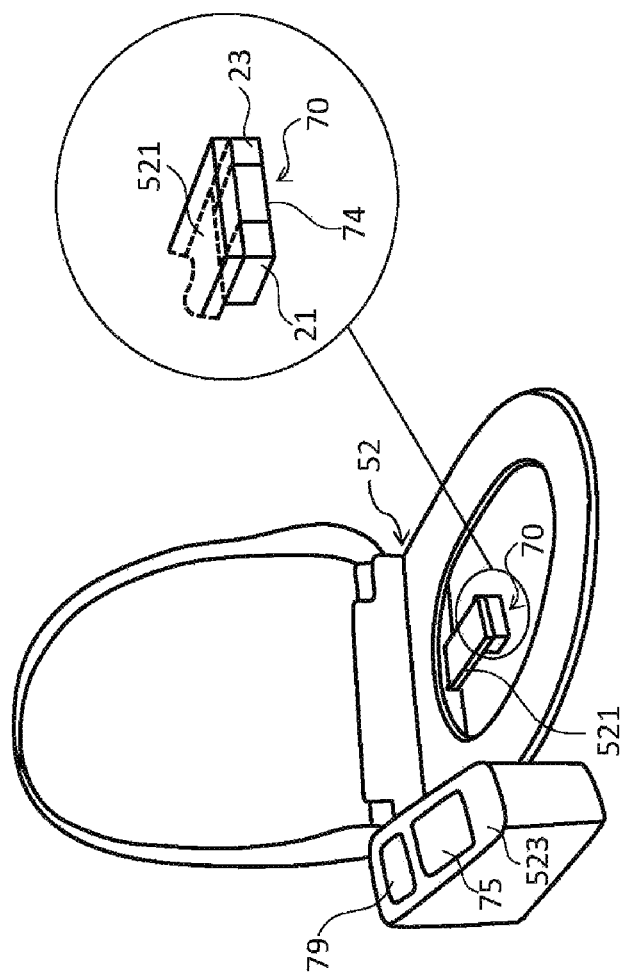
FIG. 9 is a schematic structure diagram of a stationary excreta occult blood inspection module according to another embodiment of the present invention.

FIG. 9 is a schematic structure diagram of a stationary excreta occult blood inspection module according to another embodiment of the invention. In one embodiment of the present invention, the excreta occult blood inspection apparatus 70 is applied to an electrical toilet seat 51, which comprises a wash unit 521 and a host computer 523. The case 74, the first light source 21 and the photo-sensitive unit 23 are disposed on the wash unit 521 of the electrical toilet seat 51, such as the bottom surface of the wash unit 521, and face the excreta collector 50 shown in FIG. 6, wherein the first light source 21 and the photo-sensitive unit 23 are disposed on the case 74. The user interface 79 and the display unit 75, which are independent of the case 74 and/or the wash unit 521, are not disposed on the case 74 and/or the wash unit 521. For example, the user interface 79 and the display unit 75 can be disposed on the host computer 523 of the electrical toilet seat 52, but it will not limit the scope of the rights. In different embodiment, the user interface 79 and the display unit 75 can also be installed on other portion of the electrical toilet seat 52. The analysis processor 27 can be selected to install inside or outside the case 74.

After users urinate or defecate, the wash unit 521 of the electrical toilet seat 52 will extend to prepare to perform wash process, and the case 74, the first light source 21 and the photo-sensitive unit 23, which are disposed on the bottom surface of the wash unit 521, will toward the excreta 30. At this time, users can operate the user interface 79 to start the first light source 21 up for generating the first light 213 to illuminate on the excreta 30, and then the photo-sensitive unit 23 can receive the first specimen light 302 produced by the excreta 30. Afterward the analysis processor 27 receives the detected data generated by the photo-sensitive unit 23 and analyzes the detected data to produce an analysis data. The analysis data will be sent to the display unit 75 by the analysis processor 27, and users can read the analysis data through the display unit 75.

Figure 10:
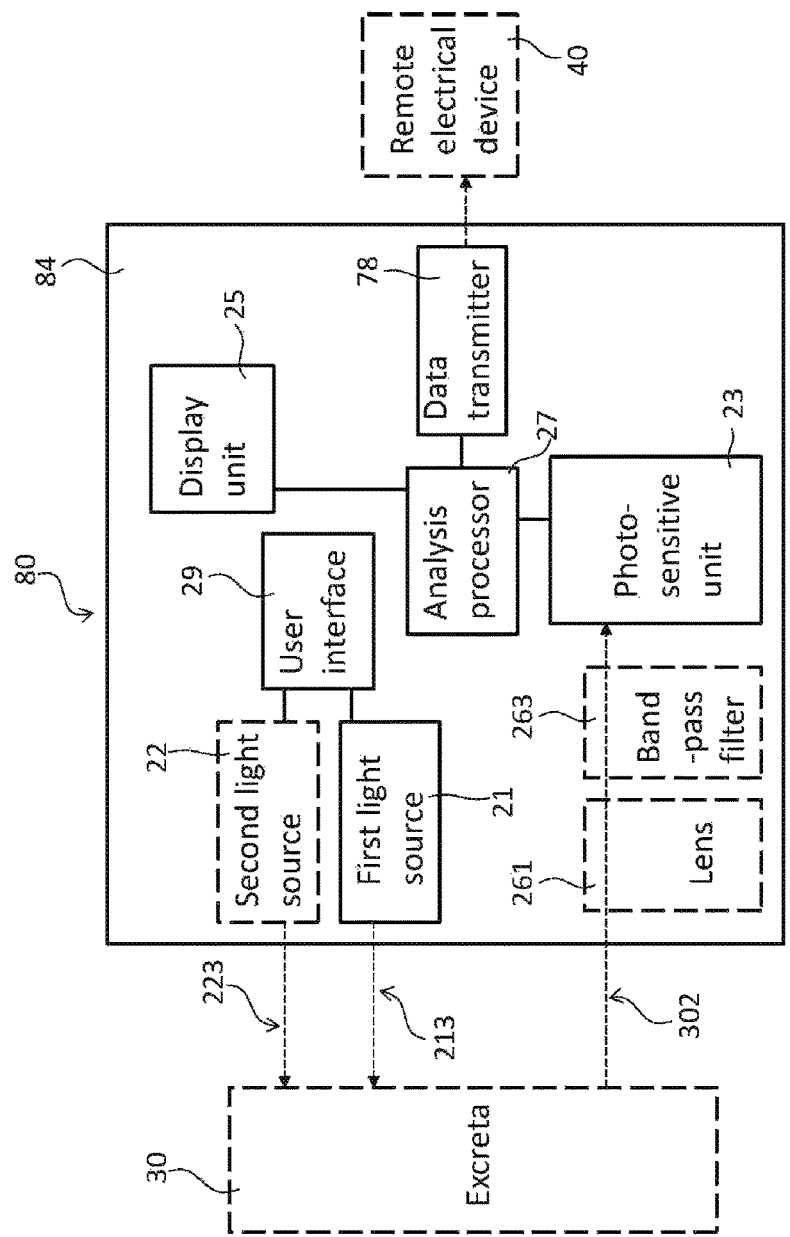
FIG. 10 is a block diagram of an excreta occult blood inspection apparatus according to another embodiment of the present invention.

FIG. 10 is a block diagram of an excreta occult blood inspection apparatus according to another embodiment of the invention. The excreta occult blood inspection apparatus 80 is similar to the excreta occult blood inspection apparatus 20 in the previous embodiment. The major difference is that the excreta occult blood inspection apparatus 80 further comprising a data transmitter 78 disposed inside the case 84, wherein the data transmitter 78 and the analysis processor 27 are electrically connected.

In one embodiment of the present invention, the data transmitter 78 can be used to send the analysis data producing by the analysis processor 27 to a remote electrical device 40. For example, the data transmitter 78 can be a wireless communication interface, such as Bluetooth, infrared or radio frequency transmitter, or a wired transmission interface, such as USB. The remote electrical device 40 can used to receive and store the analysis data. If users have a habit to do regular occult blood inspection, the remote electrical device 40 can also be used to record and track the analysis data regularly.

Figure 11:
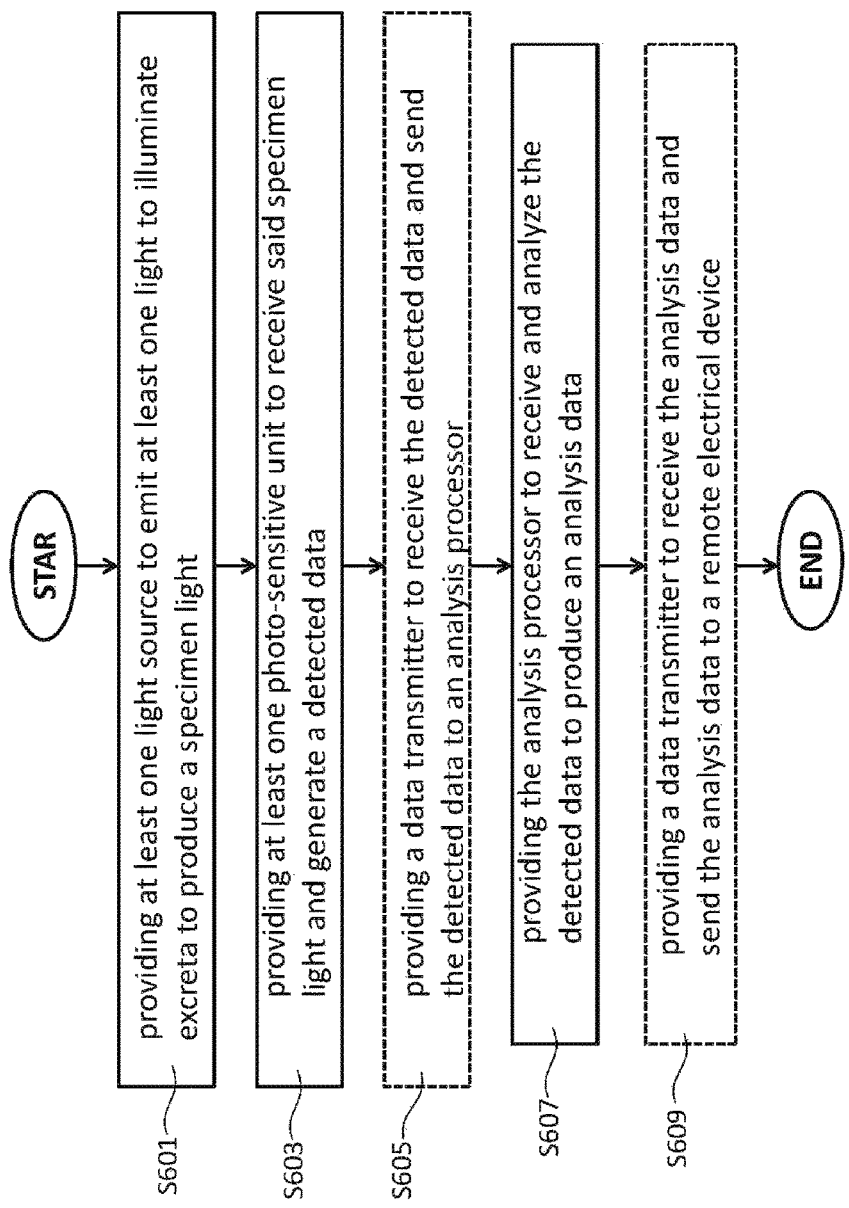
FIG. 11 is a flow chart of an excreta occult blood inspection method according to another embodiment of present invention of the present invention.

FIG. 11 is a flow chart of an excreta occult blood inspection method according to another embodiment of present invention. The excreta occult blood inspection method in this embodiment is similar to the method described in FIG. 2. The major difference is that the excreta occult blood inspection method in this embodiment is further comprises step S605 and step S609. Step S605 is performed after step S603, and a data transmitter 78 is provided to receive the detected data produced by the photo-sensitive unit 23 described in step S603 and sends the detected data to the analysis processor 77 described in step S607, as shown in step S605. In other words, step S605 is suitable to apply to the mechanism structure described in FIG. 7 to FIG. 9. Since the analysis processor 77 described in FIG. 7 to FIG. 9 is independent of the case 74, the detected data can be sent to the analysis processor 77 independent of the case 74 through the data transmitter 78.

Otherwise, step S609 in this embodiment is performed after step S607. A data transmitter 78 is provided to receive the analysis data produced by the analysis processor 27 described in step S607 and send the analysis data to the remote electrical device 40 and/or the display unit 25, as shown in step S609.

Figure 12:
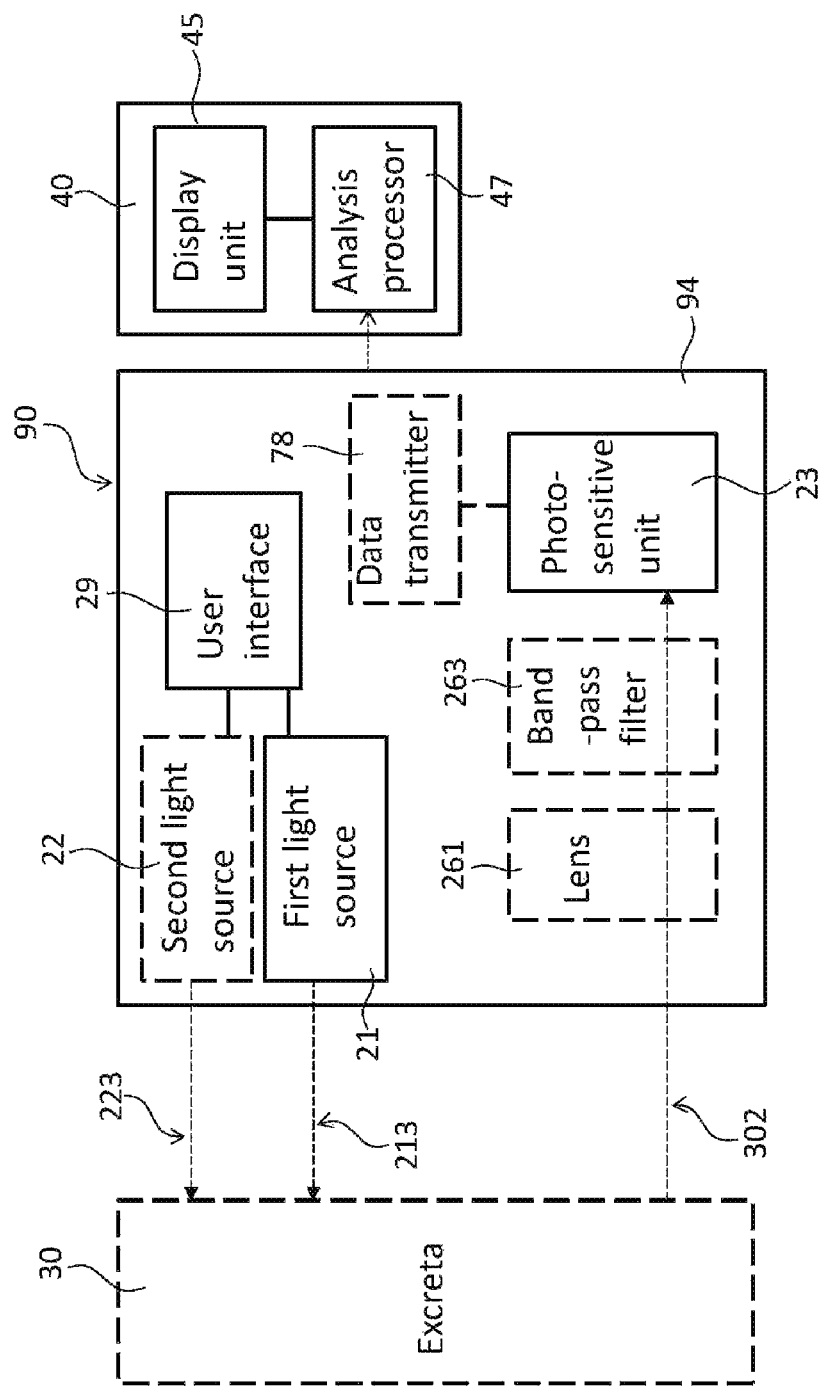
FIG. 12 is a block diagram of an excreta occult blood inspection apparatus according to another embodiment of present invention of the present invention.

FIG. 12 is a block diagram of an excreta occult blood inspection apparatus according to another embodiment of present invention. The excreta occult blood inspection apparatus 90 comprises a case 97, a first light source 21, a photo-sensitive unit 23, a user interface 29 and a remote electrical device 40. In different embodiment, the excreta occult blood inspection apparatus 90 may further comprise a second light source 22, a lens 261 and/or a band-pass filter 263. The mechanical structure and the function of the first light source 21, the photo-sensitive unit 23, the user interface 29, the remote electrical device 40, the second light source 22, the lens 261 and the band-pass filter 263 have been described in the previous embodiment, and it will not be repeated here.

The major difference between the excreta occult blood inspection apparatus 90 in this embodiment and the excreta occult blood inspection apparatus 20 described in FIG. 3 is that the excreta occult blood inspection apparatus 90 does not comprise the analysis processor 27 and the display unit 25. The analysis processor 47 of the remote electrical device 40 receives and analyzes the detected data from the photo-sensitive unit 23 for producing an analysis data, and the analysis data is received and/or displayed by the display unit 45 of the remote electrical device 40. In other words, the excreta occult blood inspection apparatus 90 only emits the first light 213 and/or the second light 223 by the first light source 21 and/or the second light 22 inside the case 94 and receives the first specimen light 302 and/or the second specimen light 304 by the photo-sensitive unit 23 inside the case 94, but the excreta occult blood inspection apparatus 90 do not perform the analysis process by the elements thereof.

Since the analysis processor 47 and the display unit 45 do not disposed inside the case 94 of the excreta occult blood inspection apparatus 90, the dimension of the case 94 can be reduced. Otherwise, the excreta occult blood inspection apparatus 90 analyzes and displays the analysis data by the existed remote electrical device 40, so the whole set-up cost of the excreta occult blood inspection apparatus 90 can be reduced efficiently.

For example, when the remote electrical device 40 is a smart phone, which can download and install an App or application program, the analysis processor 47 built-in the smart phone can analyze the received detected data according to the content of the App or application program and produce an analysis data. The analysis data will be displayed on the screen, which is the display unit 45, of the smart phone.

On the other hand, the remote electrical device 40 also can be used to store the detected data. If users have a habit to do regular occult blood inspection, the remote electrical device 40 can be used to record detected data and track the history analysis data. Each detected data can be further stored in the remote electrical device 40 and analyzed by the analysis processor 47 to produce a history analysis data.

In one embodiment of the present invention, a data transmitter 78, which is electrically connected with the photo-sensitive unit 23, can be disposed inside the case 94 and used to send the detected data produced by the photo-sensitive unit 23 to the remote electrical device 40.

The above disclosure is only the preferred embodiment of the present invention, and not used for limiting the scope of the present invention. All equivalent variations and modifications on the basis of shapes, structures, features and spirits described in claims of the present invention should be included in the claims of the present invention.

The invention claimed is:

1. An excreta occult blood inspection method for inspecting an occult blood data of excreta, comprising steps of:
   providing at least one light source to emit at least one light with a first wavelength range to illuminate said excreta to produce at least one specimen light;
   providing at least one photo-sensitive unit to receive said specimen light and generate a detected data, wherein said detected data received by said photo-sensitive unit is a spectrum; and
   providing an analysis processor to receive and analyze said detected data, capture said spectrum within a second wavelength range, and integrate said spectrum within the second wavelength range for transferring said spectrum within the second wavelength range as a light intensity value to produce an analysis data, wherein a wavelength of said first wavelength range is shorter than said wavelength of said second wavelength range.

2. The excreta occult blood inspection method according to claim 1, further comprising the step of:
   providing a data transmitter to receive said detected data and send said detected data to said analysis processor.

3. The excreta occult blood inspection method according to claim 1, further comprising the step of:
   providing a data transmitter to receive said analysis data and send said analysis data to a remote electrical device.

4. An excreta occult blood inspection apparatus for inspecting occult blood of excreta, comprising:
   a case;
   a first light source fixed on said case;
   a user interface connected with said first light source for starting said first light source up to emit a first light with a first wavelength range, wherein said first light illuminates said excreta within an excreta collector directly, and said excreta produces a first specimen light after being illuminated;
   a photo-sensitive unit fixed on said case for receiving said first specimen light and generating a detected data, wherein said detected data received by said photo-sensitive unit is a spectrum;
   an analysis processor receiving and analyzing said detected data from said photo-sensitive unit for producing an analysis data, wherein said analysis processor captures said spectrum within a second wavelength range, and integrates said spectrum within the second wavelength range for transferring said spectrum within the second wavelength range as a light intensity value, wherein a wavelength of said first wavelength range is shorter than said wavelength of said second wavelength range; and
   a display unit electrically connected with said analysis processor for displaying said analysis data.

5. The excreta occult blood inspection apparatus according to claim 4, wherein said analysis processor is disposed inside said case and electrically connected with said photo-sensitive device, and said display unit is disposed on at least one surface of said case.

6. The excreta occult blood inspection apparatus according to claim 5, further comprising a data transmitter disposed inside said case and electrically connected with said analysis processor for sending said analysis data to a remote electrical device.

7. The excreta occult blood inspection apparatus according to claim 4, wherein said analysis processor and said display unit are independent of said case, and a data transmitter disposed inside said case is electrically connected with said photo-sensitive unit for sending said detected data produced by said photo-sensitive unit to said analysis processor.

8. The excreta occult blood inspection apparatus according to claim 4, wherein said excreta with said occult blood is illuminated by said first light with said first wavelength range and generates said first specimen light with said second wavelength range.

9. The excreta occult blood inspection apparatus according to claim 8, further comprising a second light source fixed on said case for emitting a second light with a third wavelength range, wherein said second light illuminates said excreta within said excreta collector directly, wherein said excreta with said occult blood is illuminated by said second light with said third wavelength range and generates said second specimen light with a fourth wavelength range, wherein said wavelength of said third wavelength range is shorter than said wavelength of said four wavelength range.

10. The excreta occult blood inspection apparatus according to claim 4, wherein said first light is a discontinuous modulated light.

11. The excreta occult blood inspection apparatus according to claim 4, further comprising at least one lens or a band-pass filter, which are disposed on a path that said first specimen light transmits to said photo-sensitive unit.

12. The excreta occult blood inspection apparatus according to claim 4, wherein said display unit is a monitor for displaying said analysis data.

13. The excreta occult blood inspection apparatus according to claim 4, further comprising an electrical toilet seat, which comprises a host computer and a wash unit, wherein said user interface and said display unit are disposed on said host computer, and said case, said first light source and said photo-sensitive unit are disposed on said wash unit, wherein said light source and said photo-sensitive face to said excreta collector.

14. The excreta occult blood inspection apparatus according to claim 4, wherein said case is a handheld case, and said user interface is disposed on said handheld case.

15. The excreta occult blood inspection apparatus according to claim 4, further comprising a lid, wherein said display unit and said user interface is located on a first surface of said lid, and said first light source and said photo-sensitive unit is located on a second surface of said lid, wherein said first surface and said second surface are on opposite side of said lid, and when said lid is covered on said excreta collector, said first light source and said photo-sensitive unit located on said second surface face to said excreta collector.

16. An excreta occult blood inspection apparatus for inspecting occult blood of excreta, comprising:
   a case;
   a first light source fixed on said case;
   a user interface connected with said first light source for starting said first light source up to emit a first light with a first wavelength range, wherein said first light illuminates said excreta within an excreta collector directly, and said excreta produces a first specimen light after being illuminated;
   a photo-sensitive unit fixed on said case for receiving said first specimen light and generating an detected data, wherein said detected data received by said photo-sensitive unit is a spectrum; and
   a remote electrical device, comprising:
      an analysis processor disposed on said remote electrical device for receiving and analyzing said detected data from said photo-sensitive unit to generate an analysis data, wherein said analysis processor captures said spectrum within a second wavelength range, and integrates said spectrum within the second wavelength range for transferring said spectrum within the second wavelength range as a light intensity value, wherein a wavelength of said first wavelength range is shorter than said wavelength of said second wavelength range; and
      a display unit disposed on said remote electrical device and electrically connected with said analysis processor for displaying said analysis data.

17. The excreta occult blood inspection apparatus according to claim 16, further comprising a data transmitter fixed on said case and electrically connected with said photo-sensitive unit for sending said detected data produced by said photo-sensitive unit to said analysis processor.

18. The excreta occult blood inspection apparatus according to claim 16, wherein said excreta has said occult blood and generates said first specimen light with said second wavelength range.

19. The excreta occult blood inspection apparatus according to claim 18, further comprising a second light source fixed on said case for emitting a second light with a third wavelength range, wherein said second light illuminates said excreta within said excreta collector directly, wherein said excreta with said occult blood is illuminated by said second light with said third wavelength and generates said second specimen light with a fourth wavelength range, wherein said wavelength of said third wavelength range is shorter than said wavelength of said four wavelength range.

20. The excreta occult blood inspection apparatus according to claim 16, wherein said first light is a discontinuous modulated light.

\* \* \* \* \*